United States Patent
Mueller

(10) Patent No.: US 10,660,590 B2
(45) Date of Patent: May 26, 2020

(54) ARRANGEMENT HAVING A TABLET COMPUTER UNIT AND A GANTRY OF A MEDICAL IMAGING DEVICE

(71) Applicant: Siemens Healthcare GmbH, Erlangen (DE)

(72) Inventor: Hans-Juergen Mueller, Pretzfeld (DE)

(73) Assignee: Siemens Healthcare GmbH, Erlangen (DE)

( * ) Notice: Subject to any disclaimer, the term of this patent is extended or adjusted under 35 U.S.C. 154(b) by 121 days.

(21) Appl. No.: 15/939,384

(22) Filed: Mar. 29, 2018

(65) Prior Publication Data

US 2018/0279979 A1    Oct. 4, 2018

(30) Foreign Application Priority Data

Apr. 4, 2017 (EP) ..................... 17164786

(51) Int. Cl.
*A61B 6/00* (2006.01)
*G06F 1/16* (2006.01)
*A61B 6/03* (2006.01)
*H02J 50/10* (2016.01)
(Continued)

(52) U.S. Cl.
CPC ............ *A61B 6/4435* (2013.01); *A61B 6/032* (2013.01); *A61B 6/465* (2013.01); *A61B 6/467* (2013.01); *A61B 6/548* (2013.01); *G06F 1/1626* (2013.01); *G06F 1/1632* (2013.01); *G06F 1/1635* (2013.01); *G06F 1/1656* (2013.01); *H02J 50/10* (2016.02); *G16H 40/63* (2018.01); *H02J 7/025* (2013.01)

(58) Field of Classification Search
CPC ... A61B 6/4435; G06F 1/1626; G06F 1/1632; G06F 1/1635; G06F 1/1656; H02J 50/10; H02J 7/025
See application file for complete search history.

(56) References Cited

U.S. PATENT DOCUMENTS

| 9,778,691 | B2 * | 10/2017 | Sedlmair | ............... G06F 1/1632 |
| 2014/0275953 | A1 | 9/2014 | Gregerson | |
| 2015/0169001 | A1 | 6/2015 | Sedlmair | |

(Continued)

FOREIGN PATENT DOCUMENTS

| DE | 102013226342 A1 | 6/2015 |
| DE | 102014226756 A1 | 3/2016 |

(Continued)

OTHER PUBLICATIONS

German Office Action dated Apr. 10, 2019.
Extended European Search Report #17164786.0 dated Aug. 24, 2017.

*Primary Examiner* — David P Porta
*Assistant Examiner* — Fani Boosalis
(74) *Attorney, Agent, or Firm* — Harness, Dickey & Pierce, P.L.C.

(57) ABSTRACT

An arrangement includes a tablet computer unit having a tablet computer and a first connection unit and a gantry of a medical imaging device having a casing and a second connection unit. In at least one embodiment, the casing has a recess, in which the tablet computer unit can be positively mounted. Further, the second connection unit is arranged in a region of the recess such that, via the first connection unit and the second connection unit, a connection can be formed, which counteracts removal of the tablet computer unit from the recess.

22 Claims, 7 Drawing Sheets

(51) Int. Cl.
*G16H 40/63* (2018.01)
*H02J 7/02* (2016.01)

(56) References Cited

U.S. PATENT DOCUMENTS

| | | |
|---|---|---|
| 2015/0313562 A1 | 11/2015 | Kuhrt |
| 2016/0174930 A1 | 6/2016 | Braun |
| 2016/0246328 A1 | 8/2016 | Christie |
| 2016/0296197 A1 | 10/2016 | Daum |
| 2016/0367169 A1 | 12/2016 | Hardie |

FOREIGN PATENT DOCUMENTS

| | | |
|---|---|---|
| DE | 102014226287 A1 | 6/2016 |
| DE | 102015211148 A1 | 12/2016 |

\* cited by examiner

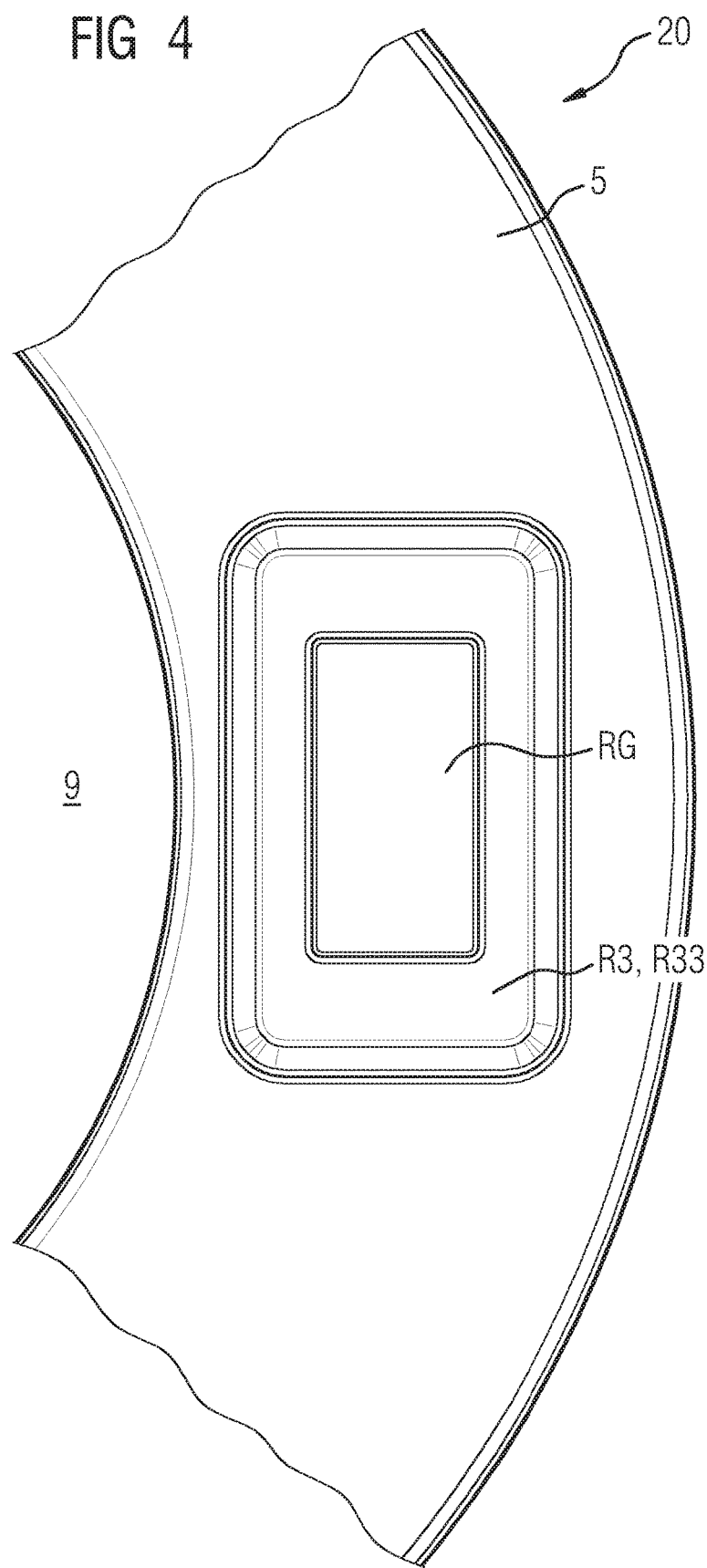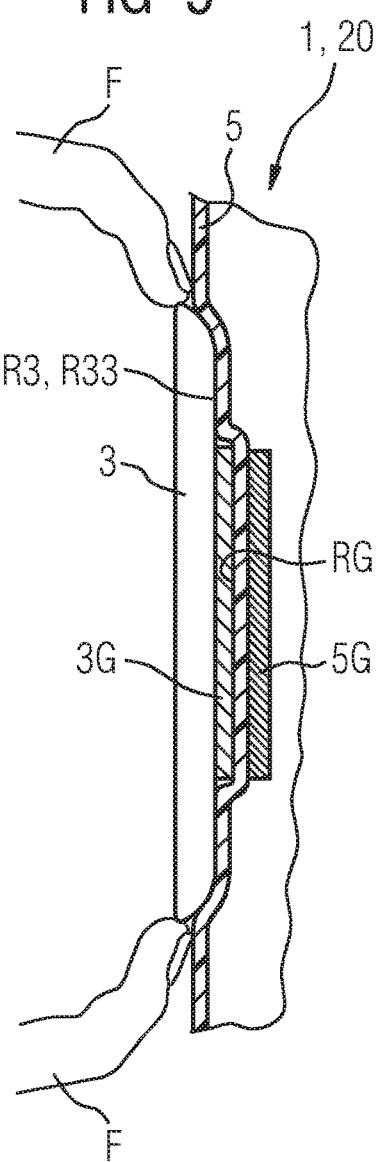

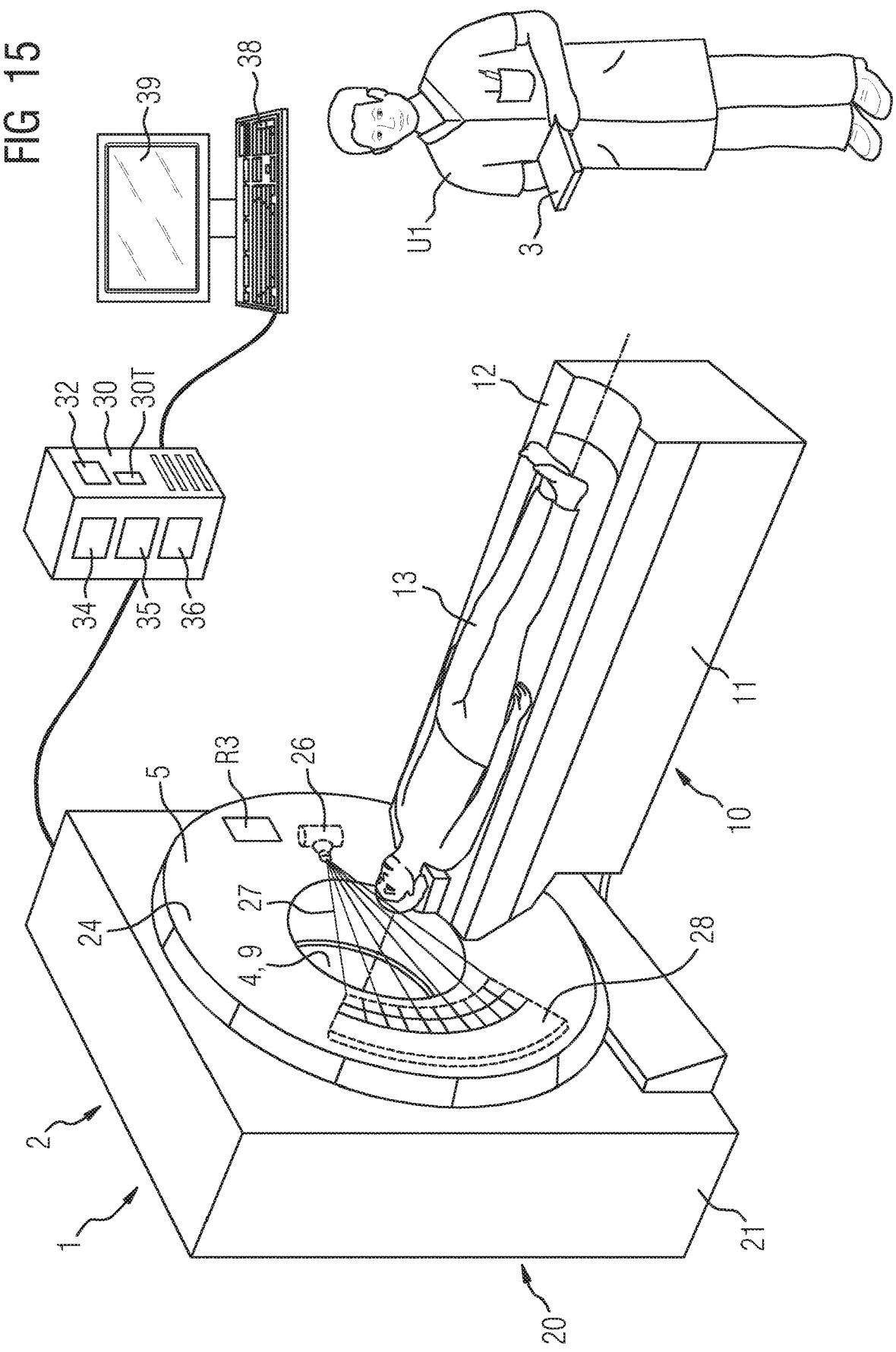

ARRANGEMENT HAVING A TABLET COMPUTER UNIT AND A GANTRY OF A MEDICAL IMAGING DEVICE

PRIORITY STATEMENT

The present application hereby claims priority under 35 U.S.C. § 119 to European patent application number EP17164786.0 filed Apr. 4, 2017, the entire contents of which are hereby incorporated herein by reference.

FIELD

At least one embodiment of the application generally relates to an arrangement including a tablet computer unit and a gantry of a medical imaging device.

BACKGROUND

Previously, computed tomography devices (CT devices) have usually been operated with the aid of operating elements, which are permanently arranged on the gantry, in particular are integrated in a casing of the gantry. Medical imaging devices can also be operated via a tablet computer. During a medical examination, which is carried out with the medical imaging device, it can be advantageous if the tablet computer can be arranged on the gantry for particular examination steps and can be used detached from the gantry for other examination steps.

DE 10 2014 226 287 A1 discloses a method for operating a medical device, having a gantry, comprising the following steps:

displaying a graphical user interface for operation of the medical device in a first output unit of a first touch-sensitive screen, inputting operating information via the graphical user interface by way of the first input unit of the first touch-sensitive screen, wherein the first touch-sensitive screen is arranged on the gantry and/or in the vicinity of the gantry.

US 2015/0169001 A1 discloses a medical technology system, having an imaging medical technology device, and having at least one portable operating/display unit, wherein the imaging medical technology device has a number of docking stations each having a closed surface, which are designed to establish a wireless data link with the operating/display unit and to simultaneously hold it in a defined position on the imaging medical technology device.

US 2015/0313562 A1 discloses a method for retrieving application commands relating to medical representation displayed on a touch-capable user interface of an arithmetic unit of a medical imaging system, at least comprising the following steps:

1.1. simultaneous touching of the user interface at at least two points of contact, and
1.2. displaying the application commands possible as a condition of the application situation on the user interface at the points of contact.

US 2016/0296197 A1 discloses a CT system for computerized tomography examination, in particular of a patient, at least having at least one mobile operating element for controlling the CT system, which is wirelessly connected to the CT system.

SUMMARY

At least one embodiment of the invention enables improved, in particular flexible, arrangement of a tablet computer unit on a gantry of a medical imaging device.

Further advantageous aspects of the invention are considered in the claims.

At least one embodiment of the invention relates to an arrangement, comprising a tablet computer unit and a gantry of a medical imaging device, wherein the tablet computer unit includes a tablet computer and a first connection unit, wherein the gantry includes a casing and a second connection unit, wherein the casing includes a recess, in which the tablet computer unit can be positively mounted, in particular is received, wherein the second connection unit is arranged in a region of the recess in such a way that, via the first connection unit and the second connection unit, a connection can be formed, which counteracts removal of the tablet computer unit from the recess.

BRIEF DESCRIPTION OF THE DRAWINGS

Selected embodiments of the invention will be illustrated below with reference to the accompanying figures. The representation in the figures is schematic, highly simplified and not necessarily to scale.

In the figures:

FIG. 4 shows a schematic diagram of a detail of an example casing of a gantry, FIG. 5 shows a schematic diagram of an example arrangement according to one embodiment of the invention, FIG. 15 shows a schematic diagram of an arrangement having a medical imaging device according to one embodiment of the invention.

DETAILED DESCRIPTION OF THE EXAMPLE EMBODIMENTS

Figure 1:
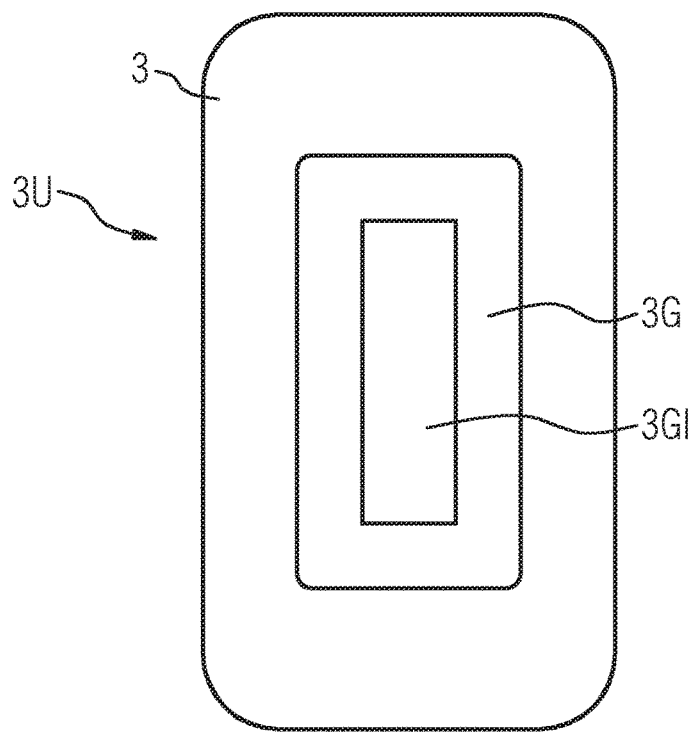
FIG. 1 shows a schematic diagram of an example tablet computer unit in a first view.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules.

Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an arrangement, comprising a tablet computer unit and a gantry of a medical imaging device, wherein the tablet computer unit includes a tablet computer and a first connection unit, wherein the gantry includes a casing and a second connection unit, wherein the casing includes a recess, in which the tablet computer unit can be positively mounted, in particular is received, wherein the second connection unit is arranged in a region of the recess in such a way that, via the first connection unit and the second connection unit, a connection can be formed, which counteracts removal of the tablet computer unit from the recess.

In particular, the recess can have a first region for positive mounting of the tablet computer and/or a second region for mounting of the first connection unit. In particular, the second region can be designed as at least one recess relative to the first region and/or as at least one opening in the first region.

In particular, the recess can have a third region, in which positive mounting of the tablet computer is interrupted in such a way that a finger and/or a tool can be applied to the tablet computer in the recess, in order to exert a compressive force for removing the tablet computer unit from the recess.

In particular, the second connection unit can be integrated in the casing and/or arranged on the casing. In particular, the second connection unit can be arranged so as to be concealed by the casing. In particular, the first connection unit can be integrated in the tablet computer and/or be arranged on the tablet computer.

In particular, the first connection unit can have at least one metal region and the second connection unit at least one magnet. In particular, the first connection unit can have at least one magnet and the second connection unit at least one metal region.

In particular, the tablet computer can have a housing with a metal housing region. In particular, the metal housing region can form the first connection unit. In particular, the metal region and/or metal housing region can be ferromagnetic. In particular, the magnet can be a permanent magnet and/or an electromagnet.

In particular, the recess can have a dock adapter, in which the tablet computer unit can be positively mounted, in particular is mounted.

In particular, the tablet computer unit can have a first power transmission element for receiving electrical power for the tablet computer. In particular, the gantry can have a second power transmission element corresponding with the first power transmission element for providing the electrical power for the tablet computer.

In particular, the first connection unit can have a plurality of, for example two, metal plates. In particular, the second connection unit can have a plurality of, for example two, magnets, which are arranged so as to correspond with the plurality of metal plates. According to one embodiment of the invention, it is provided that the first power transmission element is arranged between the two metal plates and/or that the second power transmission element is arranged between the two magnets.

In particular, the first power transmission element can have at least one first inductive element. In particular, the second power transmission element can have at least one second inductive element. An inductive element can in particular be taken to mean a coil.

In particular, the arrangement can also have a mounting tray, in which the tablet computer unit can be positively mounted, in particular is mounted, wherein the mounting tray can be arranged on a support construction independently of the gantry, wherein the mounting tray has a third connection unit, which is arranged in such a way that, via the first connection unit and the third connection unit, a connection, in particular a magnetic connection, can be formed, which counteracts removal of the tablet computer unit from the mounting tray.

In particular, the arrangement can also have the medical imaging device. The medical imaging device can for example be chosen from the imaging modalities group, which comprises an X-ray machine, a C-arm X-ray machine, a computed tomography device (CT device), a molecular imaging device (MI device), a Single Photon Emission Computed Tomography device (SPECT device), a Positron Emission Tomography device (PET device), a magnetic resonance tomography device (MR device) and combinations thereof, in particular a PET-CT device and a PET-MR device. The medical imaging device can also have a combination of an imaging modality, which is chosen for example from the imaging modalities group, and an irradiation modality. The irradiation modality can for example have an irradiation unit for therapeutic irradiation.

Without limiting the general inventive idea, a computed tomography device is cited by way of example for a medical imaging device in some of the embodiments.

According to one embodiment of the invention, the medical imaging device has an acquisition unit, which is designed for the acquisition of acquisition data. In particular, the acquisition unit can have a radiation source and a radiation detector. One embodiment of the invention provides that the radiation source is designed for emission and/or excitation of radiation, in particular electromagnetic radiation, and/or that the radiation detector is designed for detection of the radiation, in particular the electromagnetic radiation. The radiation can pass for example from the radiation source to a region for imaging and/or after interacting with the region for imaging, to the radiation detector. During interaction with the region for imaging, the radiation is modified and thereby becomes the carrier of information relating to the region for imaging. During interaction of the radiation with the detector, this information is acquired in the form of acquisition data.

In particular with a computed tomography device and with a C-arm X-ray machine, the acquisition data can be projection data, the acquisition unit a projection data acquisition unit, the radiation source an X-ray source, the radiation detector an X-ray detector. The X-ray detector can in particular be a quantum-counting and/or energy-resolved X-ray detector.

In particular with a magnetic resonance tomography device, the acquisition data can be a magnetic resonance data set, the acquisition unit a magnetic resonance date acquisition unit, the radiation source a first radio frequency antenna unit, the radiation detector the first radio frequency antenna unit and/or a second radio frequency antenna unit.

The gantry of a medical imaging device typically has a support construction, on which in particular components of the acquisition unit, in particular the radiation source and/or radiation detector, are arranged. The support construction of the gantry typically has a level of rigidity and strength such that the components of the acquisition unit can be arranged relative to each other as well as relative to a region for imaging in a geometry sufficiently defined for imaging.

With a computed tomography device, the gantry typically has a support frame and a rotor mounted so as to be rotatable relative to the support frame, with the radiation source and the radiation detector being arranged on the rotor. The gantry can optionally have a tilting frame mounted so it can be tilted relative to the support frame, wherein the rotor is arranged on the tilting frame.

With a C-arm X-ray machine, the gantry typically has a support frame and a C-arm mounted so it can be swiveled relative to the support frame, with the radiation source and the radiation detector being arranged on the C-arm.

With a magnetic resonance tomography device, the gantry typically has a support frame, on which the main magnet and a first radio frequency antenna unit are arranged, wherein the first radio frequency antenna unit is designed in the form of a body coil, which is also known to a person skilled in the art by the name "Body Coil".

At least one embodiment of the inventive solution enables in particular simple and intuitive arrangement of the tablet computer unit on the gantry and detachment of the tablet computer unit from the gantry.

In particular, it can be provided that the tablet computer unit can be positively mounted, in particular is mounted, in the recess in such a way that a surface normal of the screen of the tablet computer is essentially perpendicular, in particular is perpendicular, to a surface of the casing.

The surface of the casing can in particular be located in an edge region of the casing, which adjoins the recess, and/or which surrounds the recess.

In particular, it can be provided that the tablet computer unit can be inserted in the recess and/or can be removed from the recess in the direction of a surface normal of the screen.

In particular, the recess can have a planar bearing area. In particular it can be provided that the tablet computer unit can be positively mounted, in particular is mounted, in the recess in such a way that the tablet computer rests on the planar bearing area of the recess in a planar manner. In particular it can be provided that the tablet computer unit can be positively mounted, in particular is mounted, in the recess in such a way that the tablet computer is positively enclosed by the casing.

In particular, the casing can have a surface in the region of the recess, which surface is formed without edges and/or so as to be flat. In particular, the casing can have a surface in the region of the recess, which surface is easy to clean. This can improve the hygiene properties in the region of the recess.

In particular, the surface of the casing can be essentially closed, in particular is closed, in the region of the recess. Impairment of the rigidity and/or stability of the casing of the gantry can be avoided hereby. This kind of impairment can be caused for example by an opening in the casing. An opening of this kind can be provided for example for insertion and/or enclosure of a frame, in which a tablet computer is arranged.

In particular, it can be provided that the connection, which can be formed via the first connection unit and the second connection unit and which counteracts removal of the tablet computer unit from the recess, is a magnetic connection. In particular, the first connection unit and the second connection unit can mutually magnetically attract. A metal region can in particular be taken to mean a metal plate.

The tablet computer unit can in particular have an identification element, which is designed for identification of the tablet computer unit. According to one embodiment of the invention, it is provided that the identification element can be visually detected by a user and/or that the identification element cannot be non-destructively removed from the tablet computer. The identification element can in particular have an engraving and/or an imprint.

The tablet computer unit can have for example a metal plate with an engraving. In particular, the first connection unit can have the metal plate with the engraving. The metal plate with the engraving can in particular be ferromagnetic and/or be a connecting partner in the magnetic connection, which counteracts removal of the tablet computer unit from the recess. For example, an especially clear identification and/or allocation of the tablet computer can be achieved by way of the engraving. The metal plate having the engraving therefore forms the identification element. For example, tablet computer can be allocated via the identification element, in particular via the engraving, to a medical imaging device and/or an examination room.

For example, the dock adapter can be detachably connected, in particular is connected, to the casing of the gantry. The dock adapter can in particular have the second region for mounting the first connection unit. The dock adapter can in particular have at least one opening and/or at least one recess, which is arranged to correspond to the at least one metal region.

With the aid of dock adapters, whose form is in each case adapted to a specific model of a tablet computer, the arrangement can be flexibly adapted to different models of tablet computer.

In particular, the second power transmission element can be arranged in the region of the recess in such a way that, via the first power transfer element and the second power transfer element, a connection can be formed for transferring the electrical power for the tablet computer if the tablet computer unit is positively mounted in the recess. Wireless, in particular inductive, charging of the tablet computer is thereby possible, while the tablet computer unit is positively mounted in the recess. Compared to a solution in which a detachable plug connection on the gantry is used for the electrical power supply of the tablet computer, in particular advantages result in respect of hygiene, the mechanical stress and the speed with which the connection can be established.

The mounting tray can be designed in particular as a wall bracket for the tablet computer unit. The tablet computer unit can therefore be detached from the gantry and be mounted for example in the mounting tray. In addition, the tablet computer unit can be placed for example on a placement area, for example a table, and be operated lying on the placement area. In addition, the tablet computer unit can be operated for example by a user while the user holds the tablet computer unit in their hands. The gantry can also be developed with features which are described in conjunction with the mounting tray. Conversely, the mounting tray can also be developed with features which are described in conjunction with the gantry.

According to one embodiment of the invention, the tablet computer unit does not have a frame in which the tablet computer can be mounted, in particular is mounted, and/or to which the tablet computer can be detachably connected, in particular is connected. According to one embodiment of the invention, the tablet computer unit comprises the tablet computer and the first connection unit. According to one embodiment of the invention, the tablet computer unit comprises the tablet computer and the first connection unit and the first power transmission element.

Compared to the use of a tablet computer, which is arranged in a frame, with the frame being adapted to correspond to a holder on the gantry provided for the frame, a series of advantages can be achieved. For example, advantages result in respect of hygiene, in particular cleaning. A seal between the tablet computer and the frame must fit perfectly since otherwise liquid can penetrate between panel and frame. Cleaning is relatively complex in such a case since the frame has to be opened and be separated from the tablet computer for this purpose.

Compared to a solution in which the frame is fastened to the gantry via a tongue-and-groove system, an advantage results in respect of hygiene in particular with the magnetic connection since the tongue-and-groove system is typically a hygiene weak spot. The tablet computer can in particular be designed for operating the medical imaging device. In the context of this application, a tablet computer can also be taken to mean a panel PC, which is designed for wireless mobile use.

At least one embodiment of the invention therefore enables in particular simple, intuitive and flexible arrangement of the tablet computer unit on the gantry and detachment of the tablet computer unit from the gantry.

Use of the indefinite article "a" or "an" does not preclude the relevant feature from also being present multiple times. Use of the expression "to have" does not preclude the terms linked by way of the expression "to have" from being identical. For example, the medical imaging device has the medical imaging device. Use of the expression "unit" does not preclude the article, to which the expression "unit" refers, from having a plurality of components which are spatially separated from each other.

The use of ordinal numbers (first, second, third, etc.) in the identification of features is primarily used in the context of the present application in order to be able to distinguish the features identified by the use of ordinal numbers better. The absence of a feature, which is identified by a combination of a given ordinal number and a term, does not preclude a feature from being present which is identified by a combination of an ordinal number, which follows the given ordinal number, and the term.

FIG. 1 shows a schematic diagram of an example tablet computer unit 3U in a first view. The tablet computer unit 3U has a tablet computer 3 and a first connection unit 3G. The first connection unit 3G is a ferromagnetic metal plate having an engraving 3GI.

Figure 2:
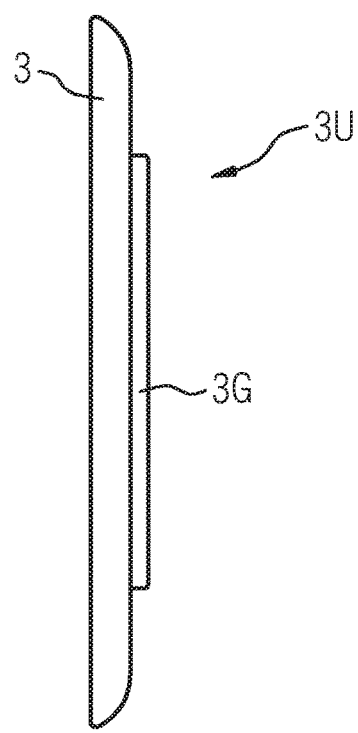
FIG. 2 shows a schematic diagram of the example tablet computer unit in a second view.

FIG. 2 shows the tablet computer unit illustrated in FIG. 1 illustrated in a second view, which is perpendicular to the first view.

Figure 3:
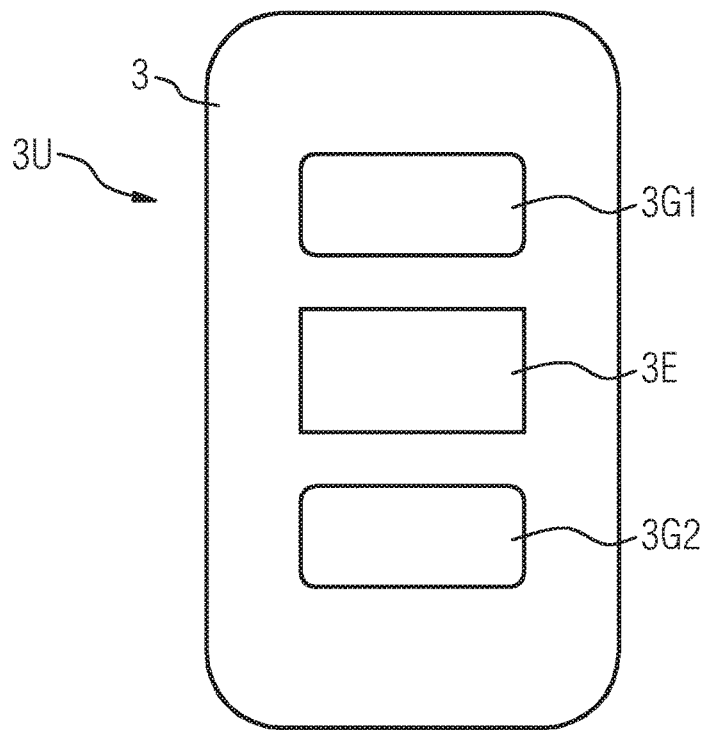
FIG. 3 shows a schematic diagram of an example tablet computer unit.

FIG. 3 shows a schematic diagram of an example tablet computer unit, with the tablet computer unit having a first connection unit, which has a first metal plate 3G1 and a second metal plate 3G2. The tablet computer unit also has a first power transmission element 3E for receiving electrical power for the tablet computer.

FIG. 4 shows a schematic diagram of a detail of an example casing 5 of a gantry 20 of a medical imaging device. The casing 5 has a recess R3, in which the tablet computer unit can be positively mounted. The recess R3 has a first region R33 for positive mounting of the tablet computer 3 and a second region RG for mounting the first connection unit 3G.

FIG. 5 shows schematic diagram of an example arrangement 1 according to one embodiment of the invention. The arrangement 1 has the tablet computer unit illustrated in FIG. 1. The arrangement 1 also has the gantry 20 having the casing 5 illustrated in FIG. 4 and a second connection unit 5G. The second connection unit 5G is a magnet, for example a permanent magnet.

The second connection unit 5G is arranged in a region of the recess in such a way that, via the first connection unit 3G and the second connection unit 5G, a connection, in particular a magnetic connection, can be formed, which counteracts removal of the tablet computer unit from the recess. A magnetic attraction acts between the first connection unit 3G and the second connection unit 5G. An edge region of the tablet computer 3, which is positively mounted in the recess, projects beyond an edge region of the casing, which adjoins the recess and which surrounds the recess in such a way that a finger F can be applied to the edge region of the tablet computer in order to exert a compressive force for removal of the tablet computer unit from the recess.

Figure 6:
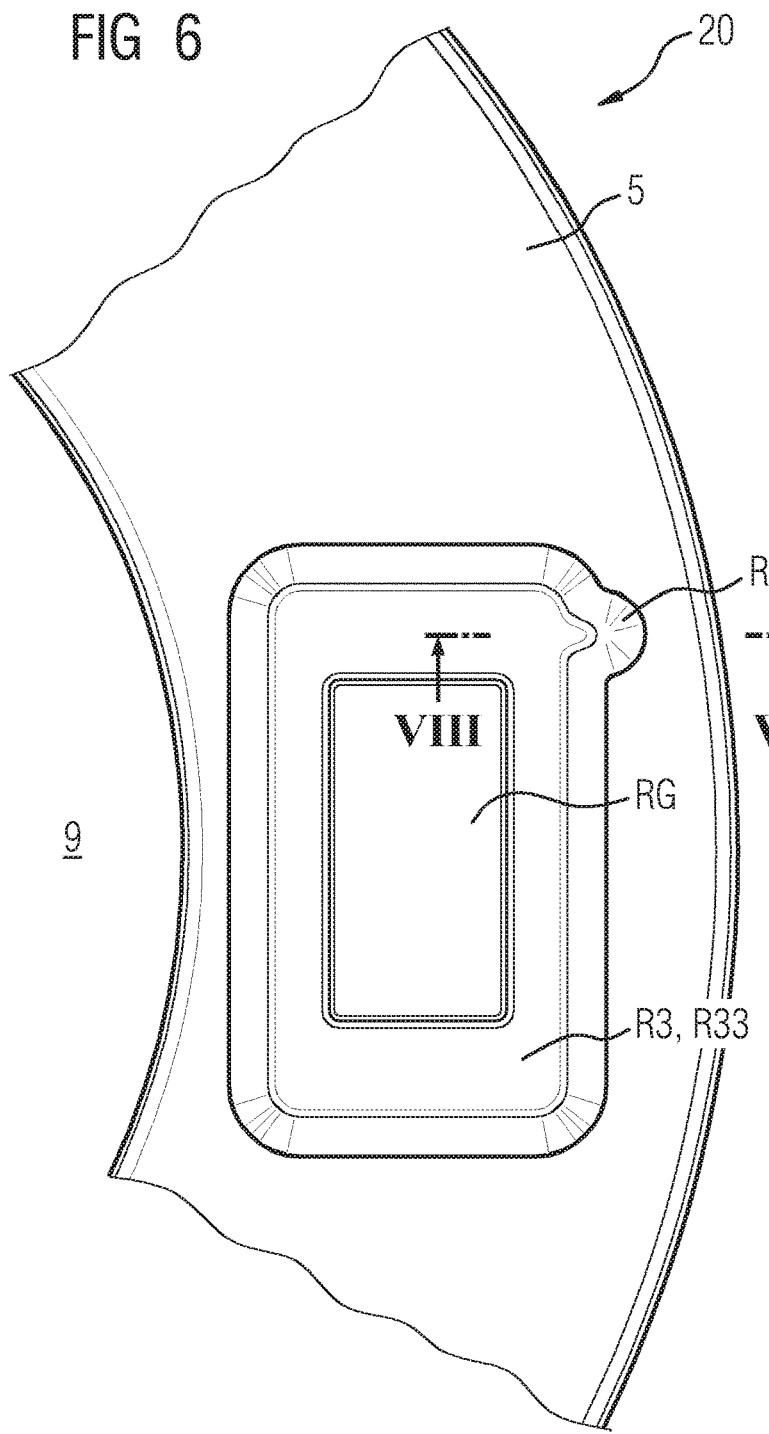
FIG. 6 shows a schematic diagram of a detail of an example casing of a gantry.

FIG. 6 shows a schematic diagram of a detail of an example casing of a gantry, with the recess having a third region RF, in which positive mounting of the tablet computer is interrupted in such a way that the finger F can be applied to the tablet computer in the recess in order to exert a compressive force for removal of the tablet computer unit from the recess.

Figure 7:
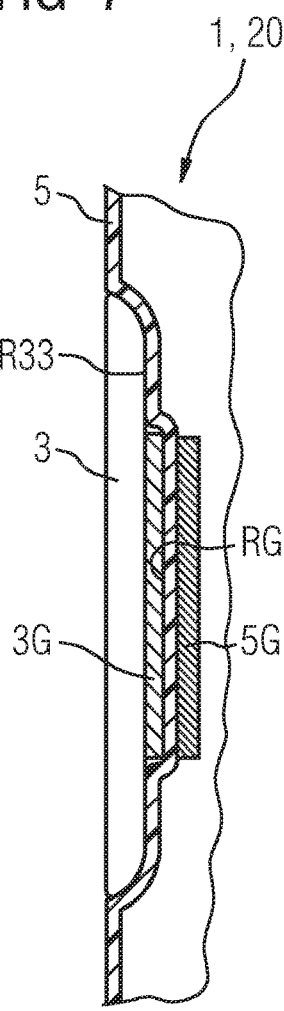
FIG. 7 shows a schematic diagram of an example arrangement according to one embodiment of the invention.

FIG. 7 shows a schematic diagram of an example arrangement according to one embodiment of the invention, with the arrangement 1 having the gantry 20 with the casing 5 illustrated in FIG. 6. The recess is designed in such a way that a screen of the tablet computer, which is positively mounted in the recess, is flush with the surface of the edge region of the casing, which adjoins the recess and surrounds the recess.

Figure 8:
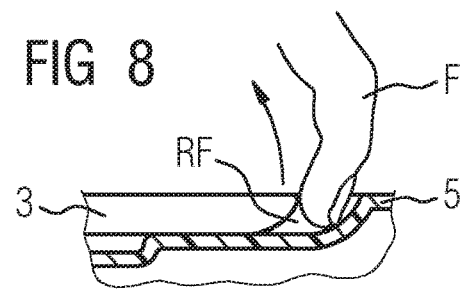
FIG. 8 shows a schematic diagram of the example arrangement along a cutting line.

FIG. 8 shows a schematic diagram of the example arrangement along the cutting line VIII-VIII in FIG. 6. A compressive force can be exerted with the finger F on the tablet computer 3 for removal of the tablet computer unit from the recess.

Figure 9:
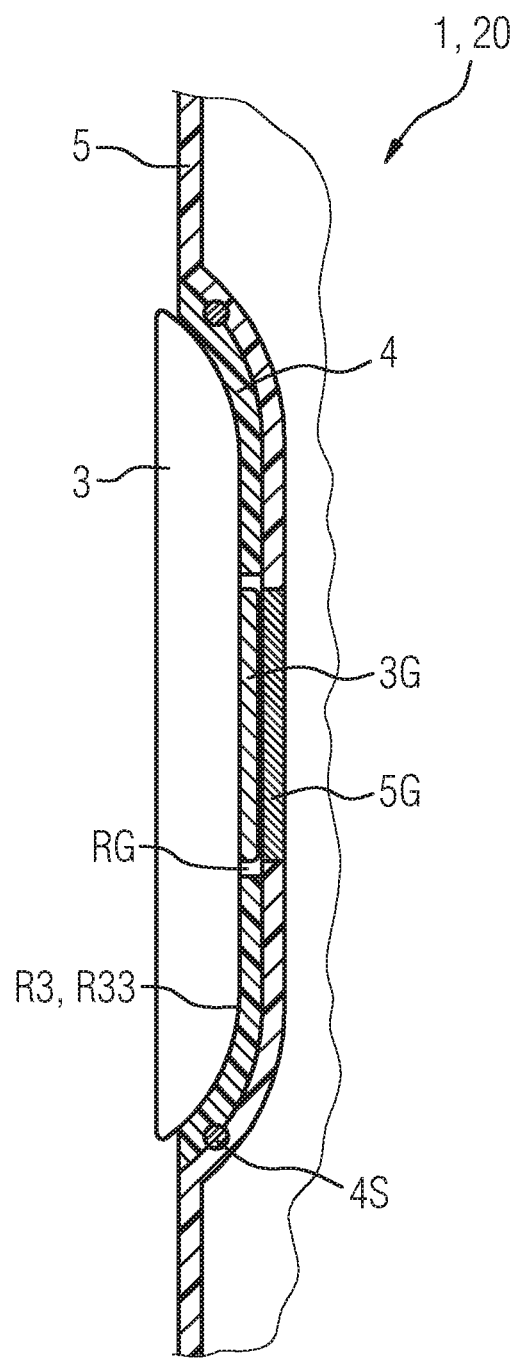
FIG. 9 shows a schematic diagram of an example arrangement having a dock adapter according to one embodiment of the invention.

FIG. 9 shows a schematic diagram of an example arrangement having a dock adapter according to one embodiment of the invention. The tablet computer unit can be positively mounted, in particular is mounted, in the dock adapter 4. The dock adapter 4 has an opening in which the first connection unit 3G can be mounted, in particular is mounted. The second connection unit 5G is integrated in the casing 5.

Figure 10:
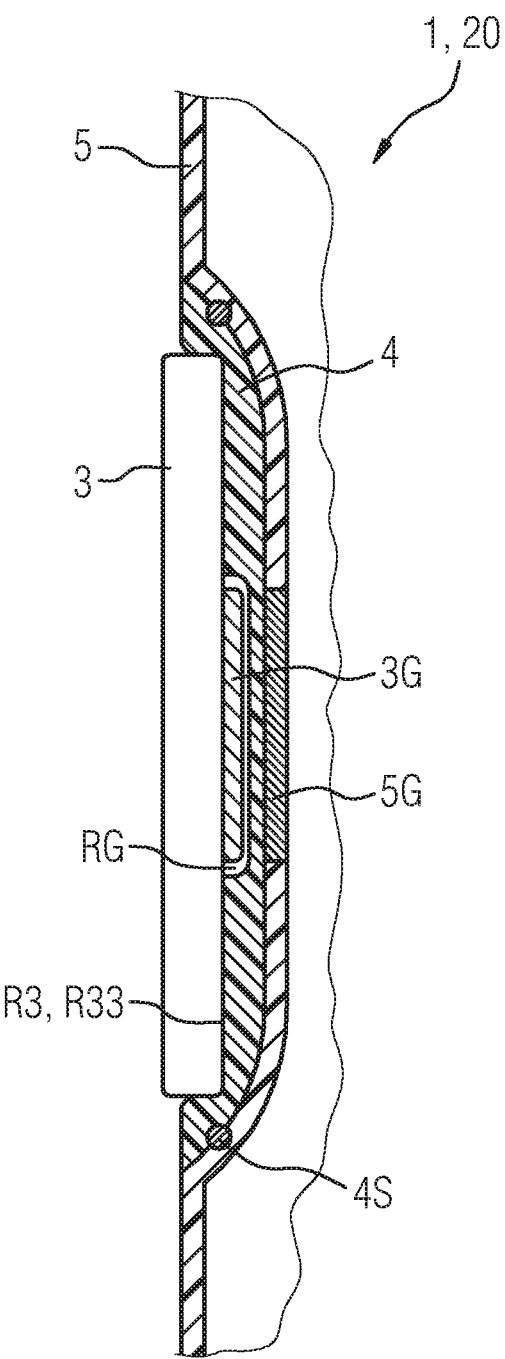
FIG. 10 shows a schematic diagram of an example arrangement having a dock adapter according to an embodiment of the invention.

FIG. 10 shows a schematic diagram of an example arrangement having a dock adapter according to one embodiment of the invention. The dock adapter 4 has a recess in which the first connection unit 3G can be mounted. The dock adapter 4 is adapted to the form of the respective tablet computer 3. The arrangement 1 can thereby be adapted to different models of tablet computer.

Figure 11:
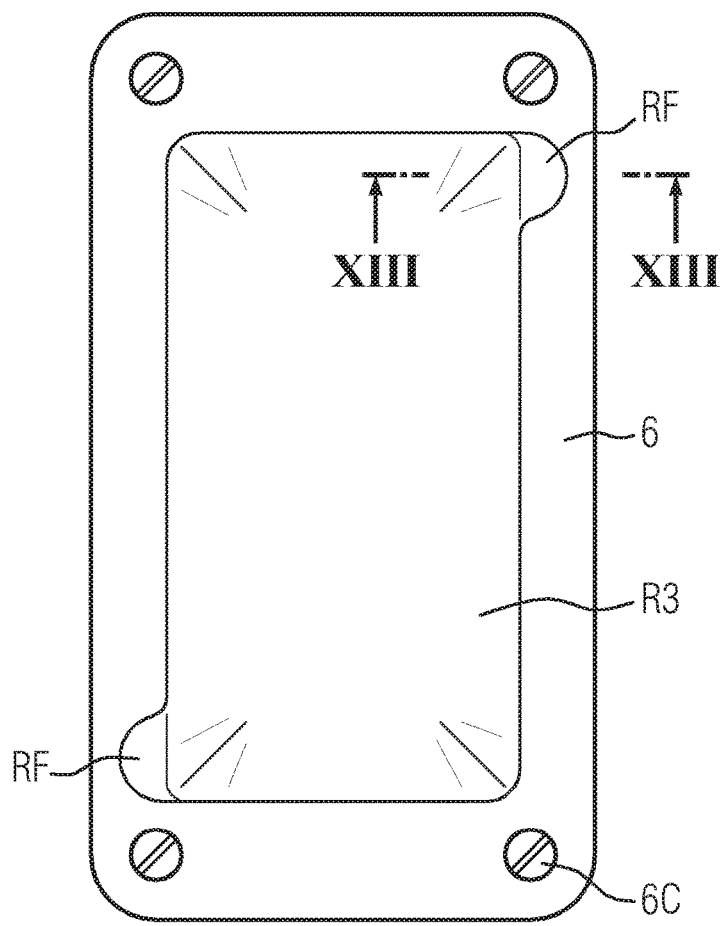
FIG. 11 shows a schematic diagram of a mounting tray in a first view.

FIG. 11 shows a schematic diagram of a mounting tray 6 in a first view. The mounting tray 6 can be secured, for example via the screws 6C, to a wall. The mounting tray 6 has a recess R3 in which the tablet computer unit can be positively mounted.

Figure 12:
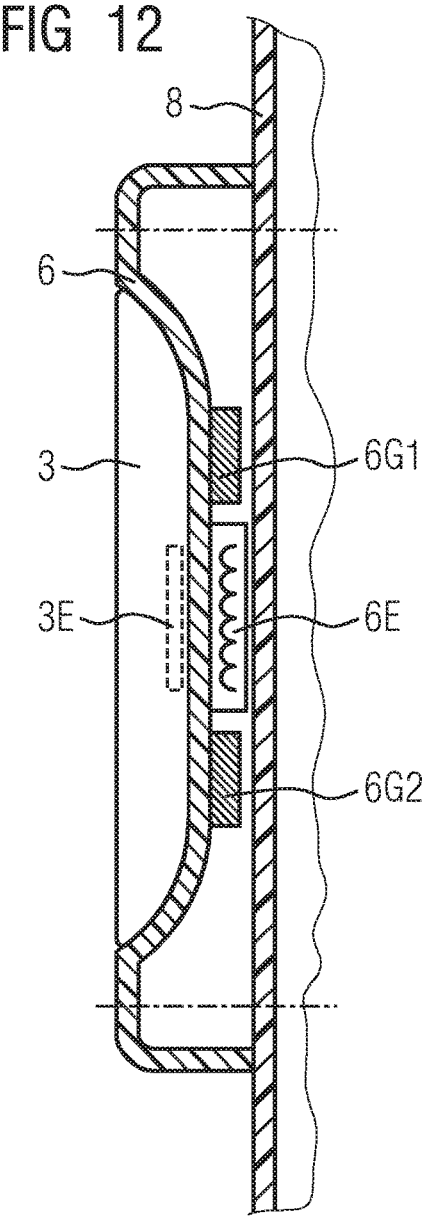
FIG. 12 shows a schematic diagram of the mounting tray in a second view.

FIG. 12 shows a schematic diagram of the mounting tray 6 in a second view. The mounting tray 6 is secured to the wall 8. The mounting tray 6 has a third connection unit, which is formed by two magnets 6G1, 6G2. The mounting tray also has an inductive element 8E in the form of a charging coil, which is arranged between the two magnets 6G1 and 6G2. The tablet computer 3 has a metal housing, which is attracted by the magnets 6G1, 6G2. The metal housing therefore forms the first connection unit. The tablet computer 3 also has an inductive element 3E in the form of a charging coil, which is arranged to correspond with the inductive element 8E. Electrical power can be transferred to the tablet computer 3 via the two inductive elements 3E, 8E, in order for example to charge a battery of the tablet computer.

Figure 13:
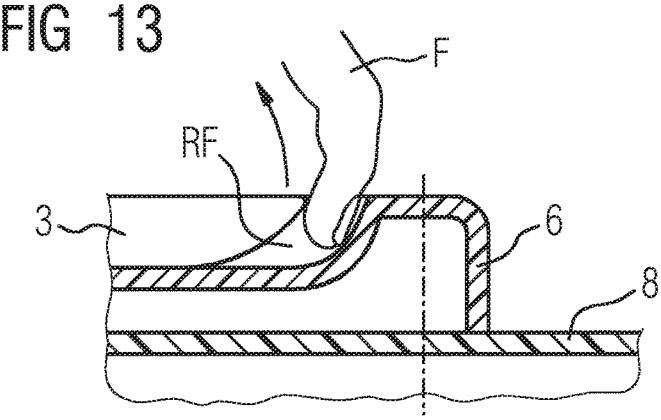
FIG. 13 shows a schematic diagram of the mounting tray along a cutting line.

FIG. 13 shows a schematic diagram of the mounting tray along a cutting line XIII-XIII in FIG. 11. A compressive force can be exerted on the tablet computer 3 with the finger F for removal of the tablet computer unit from the mounting tray.

Figure 14:
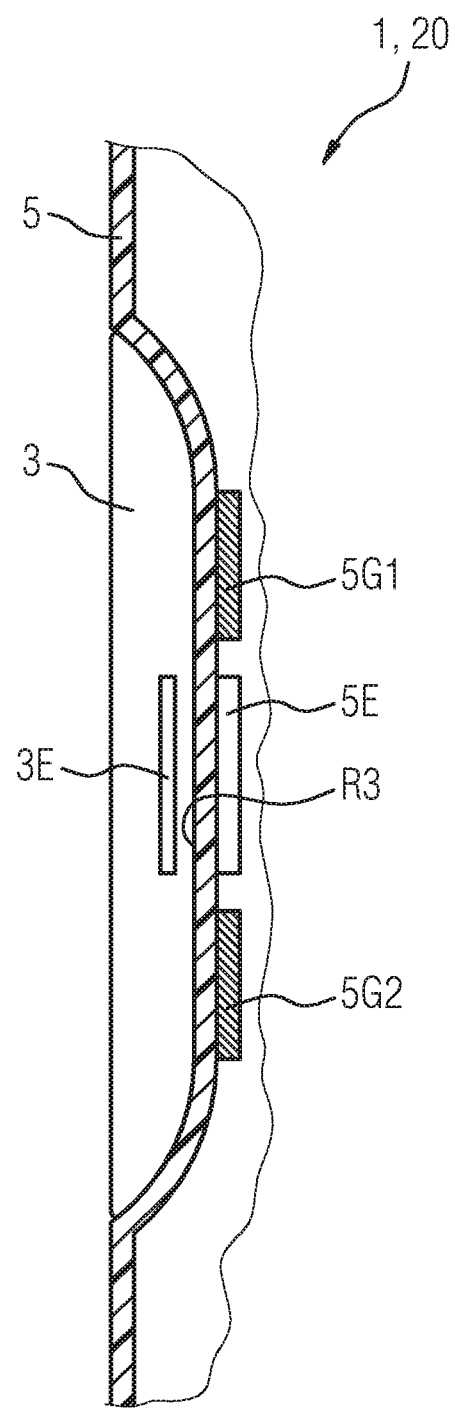
FIG. 14 shows a schematic diagram of an example arrangement according to one embodiment of the invention.

FIG. 14 shows a schematic diagram of an example arrangement 1 according to one embodiment of the invention. The tablet computer 3 has a metal housing, which is attracted by the magnets 5G1, 5G2. The metal housing therefore forms the first connection unit.

FIG. 15 shows a schematic diagram of an arrangement having a medical imaging device according to one embodiment of the invention. A computed tomography device is shown by way of example for the medical imaging device 2 without limiting the general inventive idea.

The medical imaging device has the gantry 20 with the casing 5. The casing 5 has the recess R3, in which the tablet computer unit can be positively mounted. The medical imaging device 2 also has the tunnel-like opening 9, the patient-supporting device 10 and the controller 30.

The gantry 20 has the stationary support frame 21 and the rotor 24. The rotor 24 is arranged via a pivot bearing device so as to be rotatable relative to the stationary support frame about an axis of rotation. The patient 13 is introduced into the tunnel-like opening 9. The acquisition region 4 is located in the tunnel-like opening 9. A region for imaging of the patient 13 can be positioned in the acquisition region 4 in such a way that the radiation 27 can pass from the radiation source 26 to the region for imaging and, following interaction with the region for imaging, can pass to the radiation detector 28.

The patient-supporting device 10 has the supporting base 11 and the supporting plate 12 for supporting the patient 13. The supporting plate 12 is arranged on the supporting base 11 so as to be moveable relative to the supporting base 11 in such a way that the supporting plate 12 can be introduced in a longitudinal direction of the supporting plate 12, in particular along the system axis AR, into the acquisition region 4.

The medical imaging device 2 is designed for the acquisition of acquisition data based on electromagnetic radiation 27. The medical imaging device 2 has an acquisition unit. The acquisition unit is a projection data acquisition unit having the radiation source 26, for example an X-ray source, and the detector 28, for example an X-ray detector, in particular an energy resolved X-ray detector.

The radiation source 26 is arranged on the rotor 24 and is designed with radiation quanta 27 for the emission of radiation 27, for example X-ray radiation. The detector 28 is arranged on the rotor 24 and designed for the detection of the radiation quanta 27. The radiation quanta 27 can pass from the radiation source 26 to the region for imaging of the patient 13 and, following interaction with the region for imaging, strike the detector 28. In this way, acquisition data of the region for imaging can be acquired in the form of projection data via the acquisition unit.

The controller 30 is designed for receiving the acquisition data acquired by the acquisition unit. The controller 30 is designed for controlling the medical imaging device 2. The controller 30 has the data transfer unit 30T, the computer-readable medium 32 and the processor system 36. The controller 30 is formed by a data processing system, which has a computer. Data, in particular for operating the medical imaging device, can be wirelessly transferred between the tablet computer 3 and the medical imaging device 2 via the data transfer unit 30T. The tablet computer 3 has a data transfer interface, in particular for wireless data transfer.

The arrangement 1 also has the power supply unit 35. Electrical power can be supplied to the second power transfer element 5E via the power supply unit 35. The power supply unit 35 can be for example a connection to an electrical supply network.

The controller 30 has the image reconstruction device 34. A medical image data set can be reconstructed via the image reconstruction device 34 on the basis of the acquisition data. The medical imaging device 2 has an input device 38 and an output device 39, which are each connected to the controller 30. The input device 38 is designed for inputting control information, for example image reconstruction parameters, examination parameters or the like. The output device 39 is designed in particular for outputting control information, images and/or acoustic signals. Alternatively or additionally, the control information can be input and/or output via the tablet computer 3.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An arrangement, comprising:
    a tablet computer unit including a tablet computer and a first connection unit; and
    a gantry of a medical imaging device including a casing and a second connection unit, the casing forming a first recess in which the tablet computer unit is positively mountable, and the second connection unit being in the first recess such that a first connection is formable via the first connection unit and the second connection unit, the first connection counteracting removal of the tablet computer unit from the first recess,
    wherein a first region is formed when the tablet computer unit is positively mounted, a surface of the casing and a surface of the tablet computer unit being spaced apart in the first region.

2. The arrangement of claim 1, wherein the first recess includes at least one of a second region for positively mounting the tablet computer or a third region configured to receive the first connection unit.

3. The arrangement of claim 2, wherein the first recess includes the second region and the third region, and the third region forms at least one of a second recess relative to the second region or an opening in the second region.

4. The arrangement of claim 3, wherein positive mounting of the tablet computer is interruptible using the first region by applying at least one of a finger or a tool to the tablet computer in the first region to exert a compressive force for removing the tablet computer unit from the first recess.

5. The arrangement of claim 2, wherein positive mounting of the tablet computer is interruptible using the first region by applying at least one of a finger or a tool to the tablet computer in the first region to exert a compressive force for removing the tablet computer unit from the first recess.

6. The arrangement of claim 1, wherein the second connection unit is at least one of integrated in the casing or on the casing.

7. The arrangement of claim 1, wherein the first connection unit is at least one of integrated in the tablet computer or on the tablet computer.

8. The arrangement of claim 1, wherein
    the first connection unit includes at least one metal region and the second connection unit includes at least one magnet; or
    the first connection unit includes at least one magnet and the second connection unit includes at least one metal region.

9. The arrangement of claim 1, wherein the tablet computer includes a housing including a metal housing region, and the metal housing region forms the first connection unit.

10. The arrangement of claim 8, wherein
    the at least one metal region is ferromagnetic;
    the at least one magnet is at least one of a permanent magnet or an electromagnet.

11. The arrangement of claim 1, wherein the first recess includes a dock adapter in which the tablet computer unit is positively mountable.

12. The arrangement of claim 1, wherein the tablet computer unit includes a first power transmission element configured to receive electrical power for the tablet computer.

13. The arrangement of claim 12, wherein
    the first connection unit includes two metal plates; or
    the first connection unit includes two metal plates and the first power transmission element is between the two metal plates.

14. The arrangement of claim 12, wherein the first power transmission element includes at least one first inductive element.

15. The arrangement of claim 12, wherein the gantry includes a second power transmission element corresponding with the first power transmission element, the second power transmission element configured to provide the electrical power for the tablet computer.

16. The arrangement of claim 15, wherein
    the first connection unit includes two metal plates, the first power transmission element being between the two metal plates; or
    the first connection unit includes two metal plates, the first power transmission element being between the two metal plates, and the second connection unit includes two magnets corresponding with the two metal plates, the second power transmission element being between the two magnets.

17. The arrangement of claim 15, wherein
    the first power transmission element includes at least one first inductive element; or
    the second power transmission element includes at least one second inductive element.

18. The arrangement of claim 1, further comprising:
    a mounting tray in which the tablet computer unit is positively mountable, the mounting tray being on a support construction independent of the gantry, the mounting tray including a third connection unit such that a second connection is formable via the first connection unit and the third connection unit, the second connection counteracting removal of the tablet computer unit from the mounting tray.

19. The arrangement of claim 1, further comprising: the medical imaging device.

20. The arrangement of claim 1, wherein the first recess includes a second region and a third region, and the third region forms at least one of a second recess relative to the second region or an opening in the second region.

21. The arrangement of claim 20, wherein positive mounting of the tablet computer is interruptible using the first region by applying at least one of a finger or a tool to the tablet computer in the first region to exert a compressive force for removing the tablet computer unit from the first recess.

22. The arrangement of claim 1, wherein positive mounting of the tablet computer is interruptible using the first region by applying at least one of a finger or a tool to the tablet computer in the first region to exert a compressive force for removing the tablet computer unit from the first recess.

* * * * *